United States Patent [19]

Quinn

[11] Plant 4,099

[45] Sept. 6, 1977

[54] CARNATION PLANT NAMED GEORGIA ANN

[75] Inventor: Vincent P. Quinn, Denver, Colo.

[73] Assignee: Denver Wholesale Florists Company, Denver, Colo.

[21] Appl. No.: 731,832

[22] Filed: Oct. 12, 1976

[51] Int. Cl.[2] ..... A01H 5/00

[52] U.S. Cl. ..... Plt./70

[58] Field of Search ..... Plt./70

*Primary Examiner*—Robert E. Bagwill

*Attorney, Agent, or Firm*—Chas. W. Rummler

[57] ABSTRACT

A new variety of white carnation plant of the spray type characterized by its vigorous growth and exceptionally profuse production of high centered flowers of relatively small size borne on strong upright stems and blooming continuously through the spring and fall months.

1 Drawing Figure

BACKGROUND OF THE NEW PLANT

My new carnation plant originated as a sport of an American spray type plant of unknown parentage and was discovered by me in February, 1971 among miscellaneous carnation plants of unknown parentage growing in one of my greenhouses at Denver, Colo. The apparent strength of this sport, its very attractive flower shape and color, and the many blossoms carried by the single flowering stem caused me to effect reproduction of this sport, by means of cuttings, for observation and culture and propagation of the new plant by means of cuttings through many successive generations, at Denver, Colo., has shown the novel characteristics of the plant to hold true from generation to generation and to be firmly fixed. Commercial scale asexual propagation of this new carnation plant variety is now being carried on at Denver, Colo.

DESCRIPTION OF THE DRAWING

My new variety of carnation plant is illustrated by the accompanying photographic drawing which shows flowers in full bloom and several buds in various stages of development.

DESCRIPTION OF THE NEW PLANT

The following is a detailed description of my new carnation plant based upon observations of greenhouse grown plants made at Denver, Colo., during the summer of 1976.

THE PLANT

Origin: Sport.
Parentage: A plant of unknown parentage.
Classification:
- *Botanic.*—*Dianthus caryophyllus.*
- *Commercial.*—Greenhouse carnation for cut flowers.

Form: Bush.
Height: About 85 cm.
Growth: Vigorous, sturdy, upright and precocious; 14 weeks to flower.
- *Stem size.*—About 6–7 mm. diameter and about 38 cm. long.
- *Branching.*—3 to 6 branches on original stem.

Foliage: Quantity — Abundant.
- *Size of leaf.*—Medium to small.
- *Shape of leaf.*—Lanceolate with acuminate tip. The leaves are amplexicaul and extend upwardly along the stem and then curl outwardly and downwardly.
- *Ribs and veins.*—Leaves have a prominent mid-rib.
- *Texture.*—Smooth.
- *Color.*—Upper side — Blueish-green. Under side — Yellowish-green.

THE BUD

Size: Small.
- *Diameter.*—About 14 mm. Depth: About 25 mm.

Form: Long and pointed, urn-shaped at opening.
Rate of opening: 24 to 48 hours.
Color:
- *When sepals first divide.*—White.
- *When petals begin to unfurl.*—White.

Sepals: Hooded over bud before dividing.
- *Shape.*—Lobed and pointed. Sepals stand up and do not curl back when bloom is opened.
- *Color.*—Inside — Light green. Outside — Yellowish-green.

Calyx:
- *Form.*—Funnel-shaped.
- *Aspect.*—Smooth.
- *Splitting.*—Calyx does not split.

Peduncle: Normal for spray-type carnations.
- *Strength.*—Stiff and erect.
- *Color.*—Blueish-green.

THE FLOWER

Blooming habit: Continuous and profusely from Spring through Fall.
Size of bloom: Small.
- *Diameter.*—About 63 mm.
- *Depth.*—About 43 mm.

Borne: As a spray on a sturdy stem.
Shape: Cup-shaped when bloom first opens, changing to high centered as flower matures, due to elongation of the center petals.
Petalage: Number of petals — 45 to 48 petals.
- *Arrangement.*—Alternate whorls.
- *Form.*—Fan-shaped with incised or deeply serrated and ruffled margins.
- *Texture.*—Soft.
- *Appearance.*—Satiny.
- *Color.*—Outer petals — White with a Light green base. Inside petals — White with a Light green base. Reverse sides — Same as upper side.

Petaloids: None.

Peduncle: Erect, extending sharply upward from the stem; strong and varying from about 12 to 15 cm. in length.

Persistence: Petals hang on and dry.
Fragrance: None.
Lasting quality:
*On plant.*—1 week.
*As a cut flower.*—10 to 14 days.

REPRODUCTIVE ORGANS

Stamens:
*Anthers.*—5 in number. Length: 4 mm.
*Arrangement.*—Circular about the pistils.
*Filaments.*—20 mm. long. Color: White.
*Pollen.*—Color — Greyish white.
Pistils: Number — 4.
*Styles.*—12 mm. long.

Stigmas: Color — Light greenish-white
Ovaries: One lobe per pistil.

This new variety of carnation plant is believed to be one of the highest producing white spray-type available. Its production of secondary flowers is good, providing good overall flower production quality. This plant resembles White Elegance (unpatented) in height and growth, but its flowers resemble Ocean Spray (unpatented) or White Feathers (U.S. Plant Pat. No. 2,227) in petal form.

I claim:

1. The new and distinct variety of carnation plant substantially as herein shown and described, characterized by its profuse production of white spray-type inflorescence, the flowers being of a relatively small size but high centered with alternate whorls of incised and ruffled petals.

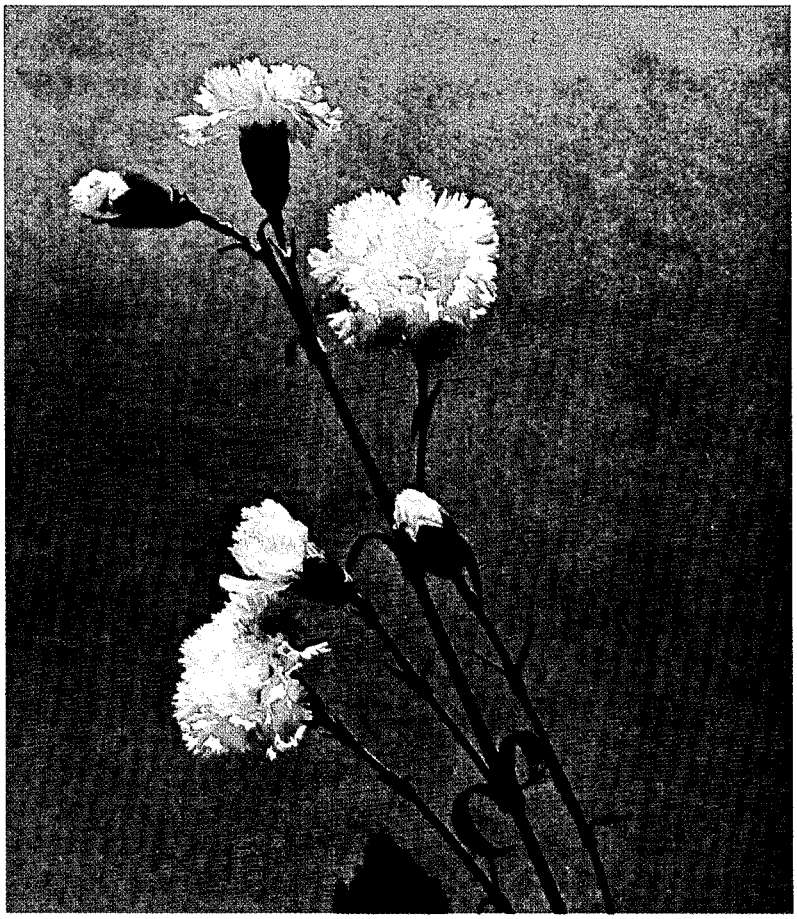

* * * * *